(12) United States Patent
Damstra et al.

(10) Patent No.: US 8,899,982 B2
(45) Date of Patent: Dec. 2, 2014

(54) IMPLANT WITH STRUCTURE FOR SECURING A POROUS PORTION

(75) Inventors: Robert Damstra, San Marcos, CA (US); Joseph A. Salvi, Chula Vista, CA (US); Shahram Zamani, Poway, CA (US); Mojtaba Esfahani, Del Mar, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 540 days.

(21) Appl. No.: 12/167,060

(22) Filed: Jul. 2, 2008

(65) Prior Publication Data

US 2010/0003640 A1   Jan. 7, 2010

(51) Int. Cl.
*A61C 8/00* (2006.01)
*A61F 2/28* (2006.01)

(52) U.S. Cl.
CPC ............ *A61C 8/0018* (2013.01); *A61C 8/0012* (2013.01); *A61C 8/0022* (2013.01)
USPC ....................................... 433/174; 623/16.11

(58) Field of Classification Search
USPC ........... 433/172–176, 201.1, 202.1, 215, 220, 433/224; 623/16.11, 20.34, 20.36, 23.34, 623/23.46; 606/301, 306, 310, 316, 321, 606/328, 331, 332
See application file for complete search history.

(56) References Cited

U.S. PATENT DOCUMENTS

| | | | |
|---|---|---|---|
| 2,721,387 A | 10/1955 | Ashuckian | |
| 3,314,420 A | 4/1967 | Smith et al. | |
| 3,423,830 A | 1/1969 | Halpern et al. | |
| 3,423,831 A | 1/1969 | Semmelman | |
| 3,497,953 A | 3/1970 | Weissman | |
| 3,685,115 A | 8/1972 | Scott | |
| 3,713,860 A | 1/1973 | Auskern | |
| 3,740,851 A | 6/1973 | Weissman | |
| 3,797,113 A | 3/1974 | Brainin | |
| 3,849,887 A | 11/1974 | Brainin | |
| 3,896,547 A | 7/1975 | Kulwiec | |
| 3,905,109 A | 9/1975 | Cohen et al. | |
| 3,906,550 A | 9/1975 | Rostoker | |
| 3,919,773 A | 11/1975 | Freeman | |
| 3,934,347 A | 1/1976 | Lash et al. | |

(Continued)

FOREIGN PATENT DOCUMENTS

| | | |
|---|---|---|
| EP | 0266313 | 5/1988 |
| EP | 0271236 | 6/1988 |

(Continued)

OTHER PUBLICATIONS

International Search Report from related application PCT/US2009/048469, Oct. 19, 2009, 9 pages.

(Continued)

*Primary Examiner* — Heidi M Eide
(74) *Attorney, Agent, or Firm* — Schwegman Lundberg & Woessner, P.A.

(57) ABSTRACT

An implant includes a head portion, an intermediate portion and an initially separate stem portion configured to engage the head portion so that at least the head portion and the stem portion cooperatively secure the intermediate portion on the implant. The implant may also include a locking mechanism configured to secure the head portion to the stem portion by a press fit or a threaded connection. The intermediate portion may include a porous metal such as tantalum.

27 Claims, 3 Drawing Sheets

(56) References Cited

U.S. PATENT DOCUMENTS

| | | |
|---|---|---|
| 3,992,725 A | 11/1976 | Homsy |
| 4,011,602 A | 3/1977 | Rybicki et al. |
| 4,016,651 A | 4/1977 | Kawahara et al. |
| 4,086,701 A | 5/1978 | Kawahara et al. |
| 4,097,935 A | 7/1978 | Jarcho |
| 4,122,605 A | 10/1978 | Hirabayashi et al. |
| 4,131,597 A | 12/1978 | Bluethgen |
| 4,178,686 A | 12/1979 | Riess et al. |
| 4,195,366 A | 4/1980 | Jarcho et al. |
| 4,199,864 A | 4/1980 | Ashman |
| 4,229,170 A | 10/1980 | Perez |
| 4,244,689 A | 1/1981 | Ashman |
| 4,252,525 A | 2/1981 | Child |
| 4,259,072 A | 3/1981 | Hirabayashi et al. |
| 4,281,991 A | 8/1981 | Michi et al. |
| 4,321,042 A | 3/1982 | Scheicher |
| 4,375,967 A | 3/1983 | Schaeffer |
| 4,379,694 A | 4/1983 | Riess |
| 4,381,918 A | 5/1983 | Ehmford |
| 4,411,624 A | 10/1983 | Ogino et al. |
| 4,431,420 A | 2/1984 | Adair |
| 4,439,152 A | 3/1984 | Small |
| 4,448,758 A | 5/1984 | Nagai et al. |
| 4,475,892 A | 10/1984 | Faunce |
| 4,478,904 A | 10/1984 | Ducheyne et al. |
| 4,483,678 A | 11/1984 | Nishio et al. |
| 4,492,577 A | 1/1985 | Farris et al. |
| 4,531,915 A | 7/1985 | Tatum, Jr. |
| 4,531,916 A * | 7/1985 | Scantlebury et al. ......... 433/173 |
| 4,536,158 A | 8/1985 | Bruins et al. |
| 4,548,959 A | 10/1985 | Nagai et al. |
| 4,556,534 A | 12/1985 | Burnett |
| 4,613,308 A * | 9/1986 | Ehrl ............................. 433/173 |
| 4,708,652 A | 11/1987 | Fujiu et al. |
| 4,713,006 A | 12/1987 | Hakamatsuka et al. |
| 4,722,688 A | 2/1988 | Lonca |
| 4,731,085 A | 3/1988 | Koch |
| 4,737,411 A | 4/1988 | Graves, Jr. et al. |
| 4,743,260 A | 5/1988 | Burton |
| 4,744,757 A | 5/1988 | Adair et al. |
| 4,744,759 A | 5/1988 | Bowen |
| 4,787,906 A * | 11/1988 | Haris .......................... 433/201.1 |
| 4,820,157 A | 4/1989 | Salvo |
| 4,842,517 A | 6/1989 | Kawahara et al. |
| 4,871,384 A | 10/1989 | Kasuga |
| 4,872,839 A | 10/1989 | Brajnovic |
| 4,872,840 A * | 10/1989 | Bori ............................. 433/173 |
| 4,877,400 A | 10/1989 | Holsclaw |
| 4,880,610 A | 11/1989 | Constantz |
| 4,906,190 A | 3/1990 | Michna |
| 4,909,738 A | 3/1990 | Ai et al. |
| 4,957,554 A | 9/1990 | Mathers et al. |
| 4,957,819 A | 9/1990 | Kawahara et al. |
| 4,960,733 A | 10/1990 | Kasuga et al. |
| 4,969,817 A | 11/1990 | Hiranuma et al. |
| 4,969,913 A | 11/1990 | Ojima |
| 4,983,182 A | 1/1991 | Kijima et al. |
| 5,000,685 A | 3/1991 | Brajnovic |
| 5,002,488 A | 3/1991 | Homsy |
| 5,004,421 A | 4/1991 | Lazarof |
| 5,007,835 A | 4/1991 | Valen |
| 5,009,709 A | 4/1991 | Ibsen et al. |
| 5,049,074 A | 9/1991 | Otani et al. |
| 5,055,497 A | 10/1991 | Okada et al. |
| 5,061,285 A | 10/1991 | Koch |
| 5,062,798 A | 11/1991 | Tsuge et al. |
| 5,064,731 A | 11/1991 | Miyazaki et al. |
| 5,076,789 A | 12/1991 | Tanaka |
| 5,087,200 A | 2/1992 | Brajnovic et al. |
| 5,120,340 A | 6/1992 | Ducheyne et al. |
| 5,123,844 A | 6/1992 | Wakai et al. |
| 5,125,839 A | 6/1992 | Ingber et al. |
| 5,125,971 A | 6/1992 | Nonami et al. |
| 5,139,424 A | 8/1992 | Yli-Urpo |
| 5,152,687 A | 10/1992 | Amino |
| 5,176,747 A | 1/1993 | Panzera et al. |
| 5,180,303 A | 1/1993 | Homburg et al. |
| 5,186,626 A | 2/1993 | Tanaka |
| 5,192,325 A | 3/1993 | Kijima et al. |
| 5,194,000 A | 3/1993 | Dury |
| 5,194,001 A | 3/1993 | Salvo |
| 5,199,873 A | 4/1993 | Schulte et al. |
| 5,205,745 A | 4/1993 | Kamiya et al. |
| 5,232,365 A | 8/1993 | Ikehara |
| 5,232,878 A | 8/1993 | Kasuga et al. |
| 5,236,458 A | 8/1993 | Ducheyne et al. |
| 5,238,405 A | 8/1993 | Marlin |
| 5,254,005 A | 10/1993 | Zuest |
| 5,282,861 A * | 2/1994 | Kaplan ...................... 623/23.51 |
| 5,282,863 A | 2/1994 | Burton |
| 5,288,232 A | 2/1994 | Panzera et al. |
| 5,306,673 A | 4/1994 | Hermansson et al. |
| 5,308,391 A | 5/1994 | Komma et al. |
| 5,310,343 A | 5/1994 | Hasegawa et al. |
| 5,312,254 A | 5/1994 | Rosenlicht |
| 5,314,334 A | 5/1994 | Panzera et al. |
| 5,342,201 A | 8/1994 | Oden |
| 5,344,318 A | 9/1994 | Wilson et al. |
| 5,344,457 A * | 9/1994 | Pilliar et al. .................. 433/174 |
| 5,346,397 A | 9/1994 | Braiman |
| 5,360,448 A * | 11/1994 | Thramann .................... 606/60 |
| 5,415,546 A | 5/1995 | Cox, Sr. |
| 5,419,702 A | 5/1995 | Beaty et al. |
| 5,425,640 A | 6/1995 | Scharf |
| 5,439,380 A | 8/1995 | Marlin |
| 5,443,515 A | 8/1995 | Cohen et al. |
| 5,449,291 A | 9/1995 | Lueschen et al. |
| 5,468,544 A | 11/1995 | Marcolongo et al. |
| 5,476,383 A | 12/1995 | Beaty et al. |
| 5,549,123 A | 8/1996 | Okuyama et al. |
| 5,554,665 A | 9/1996 | Tateosian et al. |
| 5,562,733 A | 10/1996 | Weissbach et al. |
| 5,571,016 A | 11/1996 | Ingber et al. |
| 5,572,652 A | 11/1996 | Robusto et al. |
| 5,575,652 A | 11/1996 | Gaffar et al. |
| 5,584,693 A | 12/1996 | Nishihara |
| 5,591,030 A | 1/1997 | Thiel et al. |
| 5,612,049 A | 3/1997 | Li et al. |
| 5,614,330 A | 3/1997 | Panzera et al. |
| 5,621,035 A | 4/1997 | Lyles et al. |
| 5,624,262 A | 4/1997 | Yarovesky et al. |
| 5,645,934 A | 7/1997 | Marcolongo et al. |
| 5,674,069 A | 10/1997 | Osorio |
| 5,676,745 A | 10/1997 | Kelly et al. |
| 5,683,249 A | 11/1997 | Ibsen et al. |
| 5,685,714 A | 11/1997 | Beaty et al. |
| 5,695,337 A | 12/1997 | Tyszbiat Sadoun |
| 5,697,785 A | 12/1997 | Delahaye |
| 5,697,976 A | 12/1997 | Chesterfield et al. |
| 5,697,997 A | 12/1997 | Aronsson et al. |
| 5,698,019 A | 12/1997 | Frank et al. |
| 5,713,994 A | 2/1998 | Kramer et al. |
| 5,723,007 A | 3/1998 | Engel et al. |
| 5,727,943 A | 3/1998 | Beaty et al. |
| 5,755,809 A | 5/1998 | Cohen et al. |
| 5,759,036 A | 6/1998 | Hinds |
| 5,762,500 A | 6/1998 | Lazarof |
| 5,772,438 A | 6/1998 | Deom |
| 5,775,912 A | 7/1998 | Panzera et al. |
| 5,785,524 A | 7/1998 | Wolf |
| 5,833,463 A | 11/1998 | Hurson |
| 5,833,464 A | 11/1998 | Foser |
| 5,839,900 A | 11/1998 | Billet et al. |
| 5,843,348 A | 12/1998 | Giordano |
| 5,849,068 A | 12/1998 | Hofmann et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |

(56) References Cited

U.S. PATENT DOCUMENTS

| | | |
|---|---|---|
| 5,951,290 A | 9/1999 | Ardizio et al. |
| 5,951,293 A | 9/1999 | Billet et al. |
| 5,951,295 A | 9/1999 | Lyles et al. |
| 5,964,592 A | 10/1999 | Hites et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,214,368 B1 | 4/2001 | Lee et al. |
| 6,224,662 B1 | 5/2001 | Nemeth |
| 6,244,869 B1 | 6/2001 | Billet et al. |
| 6,250,922 B1 * | 6/2001 | Bassett et al. ................ 433/172 |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,302 B1 | 1/2002 | Steidl et al. |
| 6,342,458 B1 | 1/2002 | Schweiger et al. |
| 6,343,930 B1 | 2/2002 | Beaty et al. |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 * | 9/2002 | Hollander et al. ............ 433/173 |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinghoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,999 B2 | 12/2005 | Charlebois et al. |
| 6,984,261 B2 | 1/2006 | Cummings et al. |
| 6,986,660 B2 | 1/2006 | Kumar et al. |
| 7,011,522 B2 | 3/2006 | Panzera et al. |
| 7,291,012 B2 | 11/2007 | Lyren |
| 8,057,230 B1 * | 11/2011 | Folsom, Jr. ................... 433/174 |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 * | 6/2002 | Wagner et al. ................ 433/173 |
| 2002/0095213 A1 | 7/2002 | Bakker et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0134925 A1 | 7/2003 | Guzauskas |
| 2003/0148247 A1 | 8/2003 | Sicurelli et al. |
| 2004/0024081 A1 | 2/2004 | Trieu et al. |
| 2004/0058299 A1 | 3/2004 | Molin et al. |
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 | 9/2004 | Lyren |
| 2004/0197737 A1 | 10/2004 | Uckelmann et al. |
| 2004/0234925 A1 | 11/2004 | Benhamou |
| 2004/0241614 A1 | 12/2004 | Goldberg et al. |
| 2005/0014108 A1 | 1/2005 | Wohrle et al. |
| 2005/0023710 A1 | 2/2005 | Brodkin et al. |
| 2005/0028424 A1 | 2/2005 | Poinski |
| 2005/0031704 A1 | 2/2005 | Ahn |
| 2005/0084533 A1 | 4/2005 | Howdle et al. |
| 2005/0084819 A1 | 4/2005 | Sims et al. |
| 2005/0084820 A1 * | 4/2005 | Ashman et al. ................ 433/173 |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |
| 2005/0123672 A1 | 6/2005 | Justin et al. |
| 2005/0136378 A1 * | 6/2005 | Ennajimi et al. ............. 433/173 |
| 2005/0184134 A1 | 8/2005 | Charlebois et al. |
| 2005/0191248 A1 | 9/2005 | Hunter et al. |
| 2005/0221259 A1 | 10/2005 | Anderson |
| 2005/0246021 A1 * | 11/2005 | Ringeisen et al. ......... 623/17.11 |
| 2005/0261795 A1 | 11/2005 | Ghosh et al. |

(56) References Cited

U.S. PATENT DOCUMENTS

| | | |
|---|---|---|
| 2005/0266382 A1 | 12/2005 | Soler et al. |
| 2005/0277928 A1* | 12/2005 | Boschert .................. 606/61 |
| 2006/0075826 A1 | 4/2006 | Roberts et al. |
| 2007/0015110 A1 | 1/2007 | Zhang |
| 2007/0111165 A1 | 5/2007 | Wallick |
| 2007/0118221 A1 | 5/2007 | Robie et al. |
| 2007/0148621 A1 | 6/2007 | Yakir |
| 2007/0184265 A1 | 8/2007 | Ranganathan et al. |
| 2008/0050699 A1 | 2/2008 | Zhang |
| 2008/0241793 A1 | 10/2008 | Collins |
| 2009/0036908 A1 | 2/2009 | Zokol et al. |
| 2009/0098510 A1 | 4/2009 | Zhang |
| 2009/0098511 A1 | 4/2009 | Zhang |

FOREIGN PATENT DOCUMENTS

| | | | |
|---|---|---|---|
| EP | 0366018 A1 | 5/1990 | |
| EP | 0467948 | 1/1992 | |
| EP | 0498923 | 8/1992 | |
| EP | 0560279 | 9/1993 | |
| EP | 0806211 | 11/1997 | |
| EP | 0950421 | 10/1999 | |
| EP | 1281372 | 2/2003 | |
| EP | 1598028 | 11/2005 | |
| EP | 1712205 | 10/2006 | |
| GB | 1526780 | 9/1978 | |
| GB | 2401867 | 11/2004 | |
| JP | 07255832 | 9/1995 | |
| WO | 89/00410 A1 | 1/1989 | |
| WO | 9011979 | 11/1990 | |
| WO | 9320773 | 10/1993 | |
| WO | 9421190 | 9/1994 | |
| WO | 9528973 | 11/1995 | |
| WO | 97/21393 A1 | 6/1997 | |
| WO | 9741809 | 11/1997 | |
| WO | 9830170 | 7/1998 | |
| WO | 0021455 | 4/2000 | |
| WO | 0132072 | 5/2001 | |
| WO | 0187193 | 11/2001 | |
| WO | 0236039 | 5/2002 | |
| WO | 02062901 | 8/2002 | |
| WO | 02064100 | 8/2002 | |
| WO | 03065939 | 8/2003 | |
| WO | 03065996 | 8/2003 | |
| WO | 03078508 | 9/2003 | |
| WO | 2004054464 | 7/2004 | |
| WO | 2004103202 | 12/2004 | |
| WO | WO 2006/107292 A1 * | 3/2005 | ............ A61B 17/56 |
| WO | 2006082610 | 8/2006 | |
| WO | 2007027794 | 3/2007 | |
| WO | 2007086832 | 8/2007 | |

OTHER PUBLICATIONS

An Introduction to Silanes and Their Clinical Applications in Dentistry, Jukka P.I Matinlinna et al., vol. 17, No. 2, pp. 155-164 The International Journal of Prosthodontics, 2004.

Computer-Guided Immediate Provisionalization of Anterior Multiple Adjacent Implants: Surgical and Prosthodontic Rationale, Joseph Y. K. Kan, Practical Procedures & Aethetic Dentistry, vol. 18, No. 10, 617-623, 2006.

Flocculants, Binders, and Bonds, Chapter 11, Molecular Binders pp. 173-177, 1995.

Innovative Ceramic-Fiber Technology Energizes Advanced Cerametrics, Richard B. Cass et al. Story—the American Ceramic Society, American Ceramics Society Bulletin, Nov. 2003, pp. 9701-9706.

Presurgical Planning With CT-Derived Fabrication of Surgical Guides, Scott D. Ganz, J Oral Maxillofac Surg 63:59-73, 2005, Suppl 2.

Prosthetically Directed Implant Placement ing Computer Software to Ensure Precise Placement and Predictable Prosthetic Outcomes. Part 1: Diagnostics, Imaging, and Collaborative Accountability, Alan L. Rosenfeld, International Journal of Periodontics & Restorative Dentistry, vol. 26, No. 3, 2006, 215-221.

Shape Optimization of Randomly Oriented Short Fibers for Bone Cement Reinforcements, Yan Zhou, Chaodi Li, James J. Mason, Materials Science & Engineering A 393 (2005) 374-381.

The Clinical Assessment of a Ceramic-Coated Transmucosal Dental Implant Collar; International Journal of Prosthodontics; 1996—vol. 9, Issue 5; pp. 466-472.

Two Applications of Transmucosal Milled Ceramic in Implantology; Preliminary Clinical Examples; Implant Quintessence Dentistry International; Aug. 1996—vol. 27, Issue 8, pp. 533-547.

International Search Report from related application PCT/2006/033893, dated Jan. 29, 2007, 1 page.

International Search Report from related application PCT/2006/020130, dated Feb. 6, 2007, 10 pages.

International Search Report from related application PCT/2007/069562, dated Jul. 7, 2008, 1 page.

International Search Report from related application PCT/2008/074616; dated Dec. 16, 2008; 4 pages.

International Search Report from related application PCT/2008/074645, dated Dec. 29, 2008; 9 pages.

International Search Report from related application PCT/2008/074642; dated Feb. 12, 2009, 4 pages.

International Search Report from related application PCT/2008/074655; dated Feb. 18, 2009, 9 pages.

International Search Report from related application PCT/US2009/048469; dated Oct. 19, 2009, 9 pages.

International Search Report from related application PCT/2009/048476; dated Dec. 10, 2009; 13 pages.

International Search Report from related application PCT/2009/048481; dated Dec. 10, 2009; 13 pages.

International Search Report from related application PCT/2009/062308; dated Jan. 21, 2010; 17 pages.

International Search Report from related application PCT/2009/048456; dated Apr. 27, 2010; 5 pages.

"European Application Serial No. 09774114.4, Office Action mailed Feb. 17, 2011", 2 pgs.

"European Application Serial No. 09774114.4, Response filed Mar. 28, 2011 to Office Action mailed Feb. 17, 2011", 7 pgs.

"International Application Serial No. PCT/US2009/048469, International Search Report mailed Oct. 19, 2009", 2 pgs.

"Japanese Application Serial No. 2011-516607, Office Action mailed Jul. 23, 2013", 3 pgs.

"Japanese Application Serial No. 2011-516607, Response filed Oct. 15, 2013 to Office Action mailed Jul. 23, 2013", (W/ English Translation), 24 pgs.

"Japanese Application Serial No. 2011-516607, Office Action mailed Apr. 1, 2014", (W/ English Translation), 10 pgs.

* cited by examiner

FIG. 7

IMPLANT WITH STRUCTURE FOR SECURING A POROUS PORTION

BACKGROUND OF THE INVENTION

1. Field of the Invention

The present invention relates to bone implants and, in particular, to a dental implant with structure for securing a porous portion to the implant.

2. Description of the Related Art

Dental implants are commonly used as anchoring members for dental restorations to provide prosthetic teeth at one or more edentulous sites in a patient's dentition at which the patient's original teeth have been lost or damaged. Known implant systems include a dental implant made from a suitable biocompatible material, such as titanium. The dental implant is threaded or press fit into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods.

Many current dental implant surgeries are performed in two stages. In the initial or first stage, an incision is made in the patient's gingiva at an edentulous side, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's bone grows around the implant to securely anchor the implant, a process known as osseointegration.

In a second stage of the procedure following osseointegration, the dentist reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example. Alternative single stage implants may be used that extend through the transgingival layer so that the gingiva need not be reopened to access the implant.

One way to improve osseointegration onto the implant, and in turn long term stability of the implant, is to provide a porous material on the implant that the bone can grow into. Such a porous material may also increase short term stability for immediate loading because of its large friction coefficient with surrounding bone. Securing the porous material to the dental implant, however, may be difficult due to the due to the small size and geometry of the device. In general, dental implants are 3 mm to 6 mm in diameter and 4 mm to 16 mm in length. If it is desired for the porous material to only cover a portion of the implant with the remainder being made up of, for example, reinforcing element, threads to compliment initial stability or interface geometry to secure a dental prosthesis, the porous section becomes too small to practically include threads or other securing geometry. Therefore, an implant is desired that includes a locking element to economically secure the porous material in place while allowing for other features such as threads, abutment interface geometry or reinforcing members.

DETAILED DESCRIPTION

Figures 1, 2:
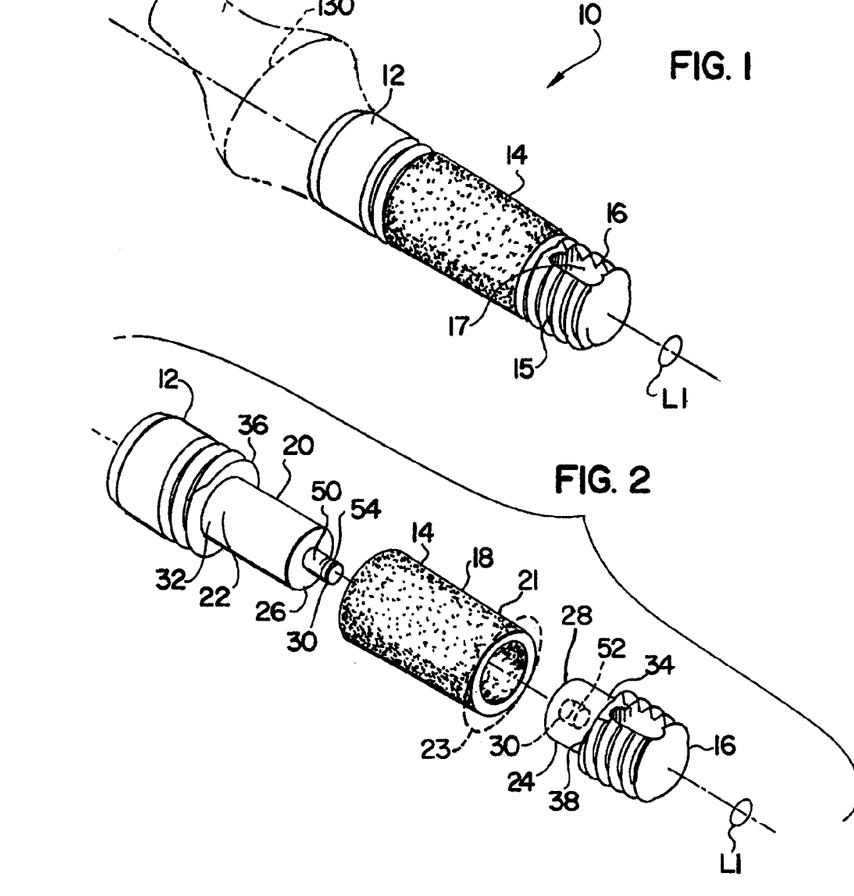
FIG. 1 is a perspective view of a dental implant with porous material in accordance with the present invention.
FIG. 2 is an exploded view of the dental implant of FIG. 1.

Referring to FIG. 1, an implant 10 for placement in bone in one form is a dental implant for insertion into a mandible or maxilla. The implant 10 comprises at least three pieces, but may include more pieces. The implant 10 is used to anchor a tooth abutment or other dental prosthesis and includes a coronal or head portion 12, an intermediate or porous portion 14 for improving osseointegration onto the implant 10 as explained in greater detail below and a separate stem or apical portion 16. The stem portion 16 is configured to engage the head portion 12 so that at least the head portion 12 and the stem portion 16 cooperatively secure the porous metal portion 14 on the implant 10.

The head portion 12 and the stem portion 16 may also comprise external threads 15 for engaging bone. Patients prefer to leave after initial surgery with some type of restoration, and healing of both soft and hard tissue may be improved if the implant is loaded after surgery. Post-surgical loading, even if less than a full load of occlusion however, is sufficient to displace the implant. Thus, self-tapping threads are used to achieve initial stability. Before osseointegration has time to take place, the thread resists tension, twisting or bending loads applied to the implant. Further, the stem portion 16 may have an opening 17 for receiving bone chips while threading implant 10 into the bone. Alternatively, the implant may be without threads to be press fit into bone by a driver and as discussed further below.

In one form, implant 10 may have an outer diameter of approximately 3.0 mm to 6.0 mm and a length of approximately 8 mm to 16 mm. While the implant 10 may have a generally cylindrical outer surface, the implant 10 may also taper so that its diameter increases as it extends coronally to further increase friction with bone within a bore receiving the implant.

Referring to FIGS. 1-2, in the illustrated form, the porous portion 14 includes a generally cylindrical sleeve portion 18 that receives and fits on a core 20 on the implant 10. The sleeve portion 18 has a thickness of about 0.020" to 0.050" and may taper to generally match the taper of the implant, if present. Alternatively, to increase the stability of the implant, the sleeve portion 18 may have an outer periphery or surface 23 (represented by dashed lines) that is non-cylindrical or non-circular (in cross-section) rather than the circular outer surface 21 that is shown. In this case, the outer surface 23 of the sleeve portion 18 does not generally match the taper or outer periphery of the implant and does not match the shape of the bore it sits within. In this case, to further strengthen the fit between the implant and the bore in the jaw bone, the outer periphery 23 of the intermediate or sleeve portion may be provided with a maximum width slightly greater than the diameter of the bore. So configured, as the implant device is inserted into the bore, the larger outer periphery roughened by the porous material will bite into the bone by grating, chipping and/or flaking bone pieces off of the sidewalls of the bore in which the implant device is being placed. When the implant is press-fit into the bore rather than threaded into the bore, this "rasping" action forms slight recesses or indents within the bore sidewall in which the implant device sits. This further restricts rotational or twisting motion of the implant device within the bore since the implant device does not have the clearance to rotate out of the indents and within the bore.

The rasping action also accelerates osseointegration onto the implant device and into the pores of the porous material due to the bone compaction into the pores. First, the grating of the bone structure causes the bone to bleed which stimulates bone growth by instigating production of beneficial cells such as osteoblasts and osteoclasts. Second, the bone pieces that fall into the pores on the porous material assist with bone remodeling. In the process of bone remodeling, osteoblast cells use the bone pieces as scaffolding and create new bone material around the bone pieces. Meanwhile osteoclast cells remove the bone pieces through resorption by breaking down bone and releasing minerals, such as calcium, from the bone pieces and back into the blood stream. The osteoblast cells will continue to replace the grated bone pieces from the pores and around the implant device with new and healthy bone within and surrounding the extraction site. Thus, with the porous material, the implant device has increased resistance to twisting or rotation, allows for immediate or very early loading, and increases long-term stability due to the improved osseointegration.

The transverse cross-section of the outer surface of the sleeve portion may have flat sides and may be polygonal, or may have curved sides such as with ovals, or may be any combination or variation thereof, whether or not a regular shape. The bore that receives such an implant may be cylindrical or any other desired predetermined shape. This applies to any of the intermediate portions described herein. The exemplary, and exaggerated, outer periphery 23 is shown to be an oval.

When assembled, the core 20 extends axially from the head portion 12, the stem portion 16, or both the head portion 12 and the stem portion 16. Core 20 also may be integrally formed with, or otherwise permanently connected to, either the head portion 12 or stem portion 16. Alternatively, core 20 may include both a coronal portion 22 which extends integrally from the head portion 12, and an apical portion 24 which extends integrally from the stem portion 16. In this case, the coronal portion 22 and the apical portion 24 may have engaging distal ends 26 and 28 that form a locking mechanism 30 configured to secure the head portion 12 to the stem portion 16. As another alternative, however, the core 20 may have one longitudinal end 32 integral with one of the head and stem portions 12 and 16, and an opposite longitudinal end 34 forming locking mechanism 30 to engage with the other of the head and stem portions 12 and 16.

As yet another alternative, the core 20 is separate (or has a separate portion) from both the head portion 12 and the stem portion 16. In this form, a locking mechanism 30 is formed at both opposite longitudinal ends 32 and 34 of the core (or at two other intermediate locations along the core).

To secure the sleeve portion 18 on the core 20, the head and stem portions 12 and 16 have a greater diameter than the core 20 such that the head portion 12 and the stem portion 16 each have a retaining shoulder 36 and 38 that extends radially outward from the core 20 relative to a longitudinal axis L1 generally defined by the implant 10. The shoulders 36 and 38 face each other so that when sleeve portion 18 is assembled on the core 20, the sleeve portion 18 is retained between the shoulders 36 and 38.

In one form, the head portion 12, the stem portion 16 and the core 20 (whether or not it is separate) are made of a suitable biocompatible material such as titanium, titanium alloy, stainless steel, zirconium, cobalt-chromium molybdenum alloy, polymers such as polyether ketone ketone (PEKK) for one example, ceramic, and/or composite material.

Figure 3:
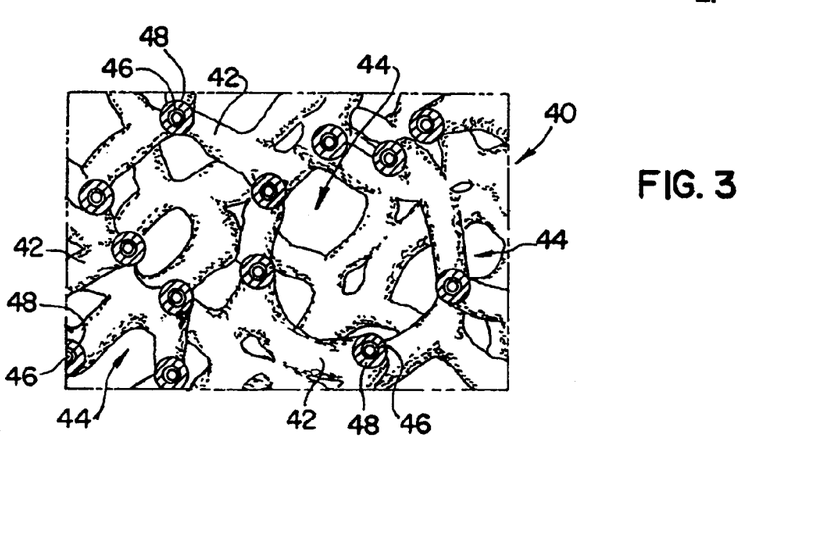
FIG. 3 is an enlarged fragmentary view of a porous tantalum portion for any of the embodiments herein and in accordance with the present invention.

Referring to FIG. 3, the porous portion 14 may include metal, and in one form, is a porous tantalum portion 40 which is a highly porous biomaterial useful as a bone substitute and/or cell and tissue receptive material. An example of such a material is produced using Trabecular Metal™ technology generally available from Zimmer, Inc. of Warsaw, Ind. Trabecular Metal™ is a trademark of Zimmer Technology, Inc. Such material may be formed from a reticulated vitreous carbon foam substrate which is infiltrated and coated with a biocompatible metal, such as tantalum, etc., by a chemical vapor deposition ("CVD") process in a manner disclosed in detail in U.S. Pat. No. 5,282,861, the disclosure of which is fully incorporated herein by reference. Other metals such as niobium or alloys of tantalum and niobium with one another or with other metals may also be used.

As shown in FIG. 3, porous tantalum structure 40 includes a large plurality of ligaments 42 defining open spaces 44 therebetween, with each ligament 42 generally including a carbon core 46 covered by a thin film of metal 48 such as tantalum, for example. The open spaces 44 between ligaments 42 form a matrix of continuous channels having no dead ends, such that growth of cancellous bone through porous tantalum structure 40 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor implant 10 into the surrounding bone of a patient's jaw which increases stability. The rough exterior surface of such porous metal portion has a relatively high friction coefficient with adjacent bone forming the bore that receives the implant to further increase initial stability as alluded to above. This structure can produce superior aesthetic results by restricting movement of the implant. These implants can be placed without supplementary surgical procedures, such as bone grafting, and can be placed in areas where traditional implants have been less successful, such as with reduced or decayed alveolar sections.

Porous tantalum structure 40 may be made in a variety of densities in order to selectively tailor the structure for particular applications. In particular, as discussed in the above-incorporated U.S. Pat. No. 5,282,861, the porous tantalum may be fabricated to virtually any desired porosity and pore size, whether uniform or varying, and can thus be matched with the surrounding natural bone in order to provide an improved matrix for bone in-growth and mineralization. This includes a gradation of pore size on a single implant such that pores are larger on an apical end to match cancellous bone and smaller on a coronal end to match cortical bone, or even to receive soft tissue ingrowth. Also, the porous tantalum could be made denser with fewer pores in areas of high mechanical stress. Instead of smaller pores in the tantalum, this can also be accomplished by filling all or some of the pores with a solid material which is described in further detail below.

To provide additional initial mechanical strength and stability to the porous structure, the porous structure may be infiltrated with a filler material such as a non-resorbable polymer or a resorbable polymer. Examples of non-resorbable polymers for infiltration of the porous structure may include a polyaryl ether ketone (PAEK) such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone.

Examples of resorbable polymers may include polylactic co-glycolic acid (PLGA), polylactic acid (PLA), polyglycolic acid (PGA), polyhydroxybutyrate (PHB), and polyhydroxyvalerate (PHV), and copolymers thereof, polycaprolactone, polyanhydrides, and polyorthoesters. By providing additional initial mechanical strength and stability with a resorbable filler material, a titanium reinforcing implant core may not be required. The resorbable material would resorb as the bone grows in and replaces it, which maintains the strength and stability of the implant.

Referring again to FIGS. 1-2, the locking mechanism 30 may secure the head and stem portions 12 and 16 together by a threaded connection, press fit, or similar mechanisms. Thus, the locking mechanism 30 may include at least one axially extending post 50 on either the core portion 22 of the head portion 12 or core portion 24 of the stem portion 16. An axially extending bore 52 (shown in dashed line) receives the post 50 on the other core portion 22 or 24. In the illustrated form, the post 50 may have threads 54 to match internal threads in bore 52. Otherwise, the post 50 may have a corresponding diameter to provide a tight friction fit to be press fit into bore 52.

With this configuration, the head portion 12 and stem portion 16 secure the sleeve portion 18 on the core 20 without other devices. It will be appreciated, however, that the sleeve portion 18 could additionally be dimensioned to have a friction fit on the core 20 to resist further axial and/or rotational movement of the sleeve portion 18 on the core 20. Other mechanisms, such as adhesive, welding, diffusion bonding, sintering, fasteners, and so forth may also be used to secure the sleeve portion 18 to the core 20.

It will also be understood that head portion 12 may have a male abutment connector on its coronal surface to connect to a separate abutment. Alternatively, the head portion 12 has a bore for receiving a portion of an abutment and/or an abutment anchor where such bore may also extend into the core 20.

Figures 4, 5, 6:
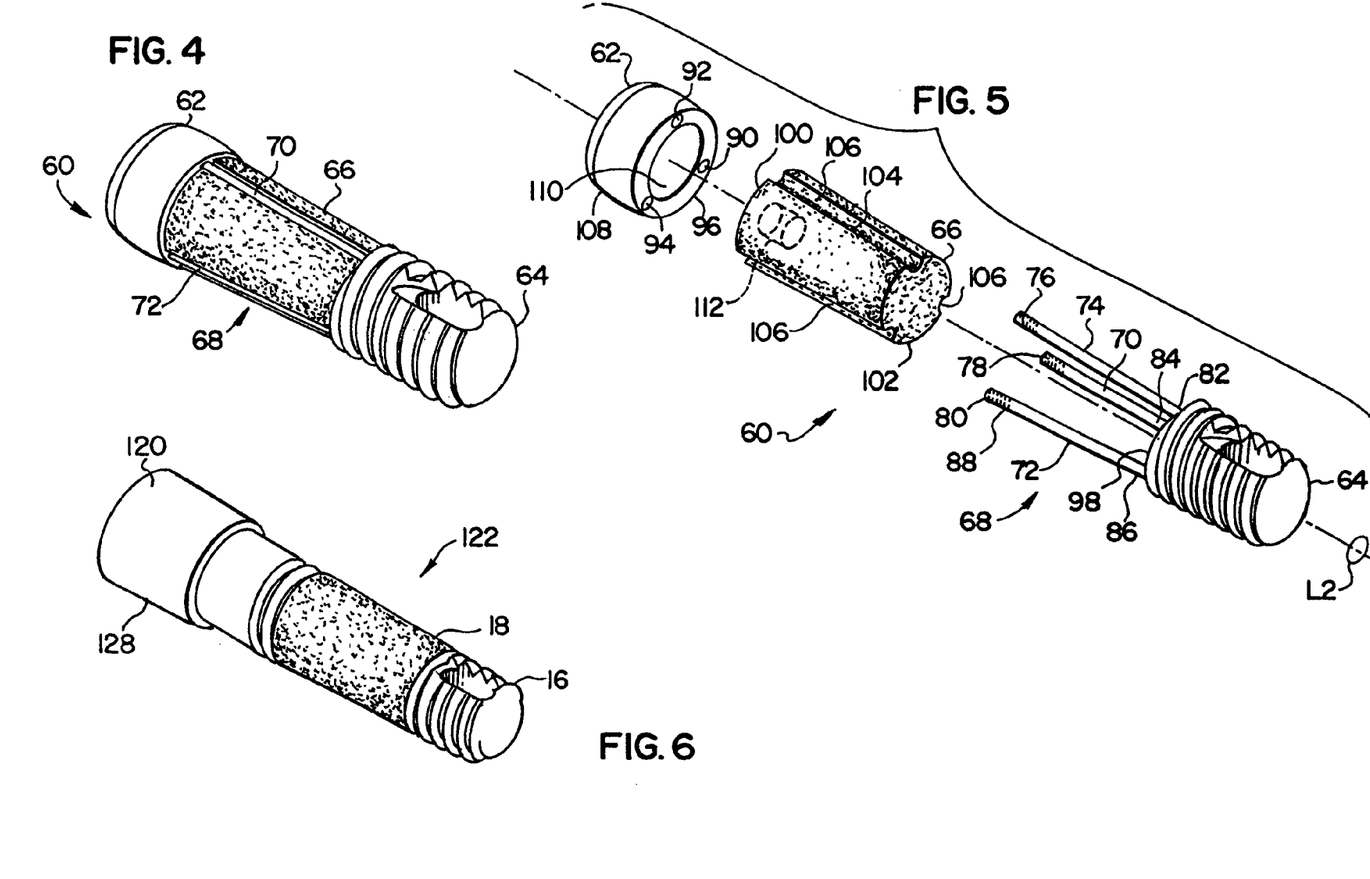
FIG. 4 is a perspective view of a second embodiment of a dental implant in accordance with the present invention.
FIG. 5 is an exploded view of the dental implant of FIG. 4.
FIG. 6 is a perspective view of a third embodiment of a dental implant in accordance with the present invention.

Referring now to FIGS. 4-5, implant 60 has a similar basic structure to that of implant 10 including a head portion 62 and a stem portion 64 that cooperatively secures a porous portion 66 to the implant 60. Porous portion 66 has the same or similar material as porous portion 14 on implant 10. A locking mechanism 68 secures the head portion 62 to the stem portion 64. The locking mechanism 68 here, however, includes a plurality of locking members 70, 72 and 74 that extend axially from the head portion 62 and the stem portion 64. Each locking member 70, 72 and 74 has an end portion 76, 78, 80, respectively, that engages the head portion 62, and respective end portions 82, 84, 86 that engage the stem portion 64. In one form, the end portions 76, 78, 80 or end portions 82, 84, 86 are integrally formed with either the head portion 62 or stem portion 64 while the opposite end portions are free ends that engage the head portion 62 or the stem portion 64 by either a press fit or by a threaded connection with threads 88 (shown in dashed lines). In this case, the free end portions, whether configured for press-fit or threaded connections, are respectively received in bores 90, 92, and 94. It will be understood, however, that all of the end portions 76, 78, 80 and 82, 84, 86 may be free ends that fit into bores on both the head portion 62 and the stem portion 64. If threaded connections are used, bores 90, 92, and 94 may be through bores so that the locking members 70, 72, and 74 may be independently rotated into place and anchored to stem 64 (or vice-versa).

In the illustrated form, the three locking members 70, 72, and 74 are uniformly, circumferentially spaced about central longitudinal axis L2, and the porous portion 66 is centrally located among the locking members 70, 72, and 74 so that the locking members restrict lateral movement of the porous portion 66 while interior faces 96 and 98 of the head and stem portions 62 and 64, respectively, face or abut longitudinal ends 100 and 102 of the porous portion 66 to restrict axial movement of the porous portion 66.

To further restrict rotational and lateral movement of the porous portion 66, the porous portion 66 may have an outer surface 104 defining at least one longitudinally extending groove 106 for receiving the locking members 70, 72 and 74. In the illustration, the outer surface 104 defines a groove 106 for each locking member 70, 72 and 74.

The porous portion 66 separates the head portion 62 from the stem portion 64 except for the locking members 70, 72 and 74. The porous portion 66 may be a bulk piece that is substantially porous. When implant 60 has a taper, the exterior surface 104 and/or the locking members 70, 72, and 74 may be inclined to match the slope of the taper. For this purpose, the locking members 70, 72, and 74 may also extend radially outwardly as the locking members 70, 72 and 74 extend coronally. It will be understood that instead, the locking members 70, 72 and 74 may remain parallel to axis L2 while the outer surface 104 tapers, or vice versa.

It will be appreciated that the locking mechanism 68 may have as few as one off-center locking member or more than three locking members whether or not uniformly spaced from and/or about longitudinal axis L2.

It will also be understood that while the locking mechanism 68 may secure the porous portion 66 to the implant 60 alone, adhesive, welding, diffusion bonding, sintering, fasteners and the like between the porous portion 66 and the locking members 70, 72 and 74, head portion 62 and/or stem portion 64 may also be used.

The head portion 62 of implant 60 may include a collar 108. The collar 108 forms face 96 as an apically facing annular side. An interior surface 110 formed by a collar 108 extends coronally from the face 96 and is configured for receiving an abutment connector. Porous portion 66 may have a corresponding bore 112 (shown in dashed line) that aligns with interior surface 110 to receive a portion of a separate abutment and/or an abutment connector. The bore 112 may or may not be threaded. Alternatively, the head portion 12 includes male structure to mount a separate abutment.

Implant 60 may be an externally threaded implant rather than a press fit implant. In this case, stem portion 64 may have similar structure as that of stem portion 16 on the implant 10 relating to threading and self-tapping. While the collar 108 is shown without external threads, it will be understood that such threads could be provided.

It will be understood that porous portions 14 and 66 could be formed with external threads continues with threads of the head and/or stem portions. With implant 60, the locking members 70, 72 and 74 may or may not have shapes to match the threads.

It will also be appreciated that for any of the configurations herein, the intermediate sleeve or bulk material may be made of, or include, materials that promote bone growth or increase the strength of the implant other than porous tantalum. Such materials include organic bone graft (e.g., autograft, allograft, xenograft), resorbable polymer (e.g., polylactic co-glycolic acid (PLGA), polylactic acid (PLA), polyglycolic acid (PGA), polyhydroxybutyrate (PHB), and polyhydroxyvalerate (PHV)), non-resorbable polymer, synthetic bone material such as hydroxyapatite (HA), or collagen.

Figure 7:
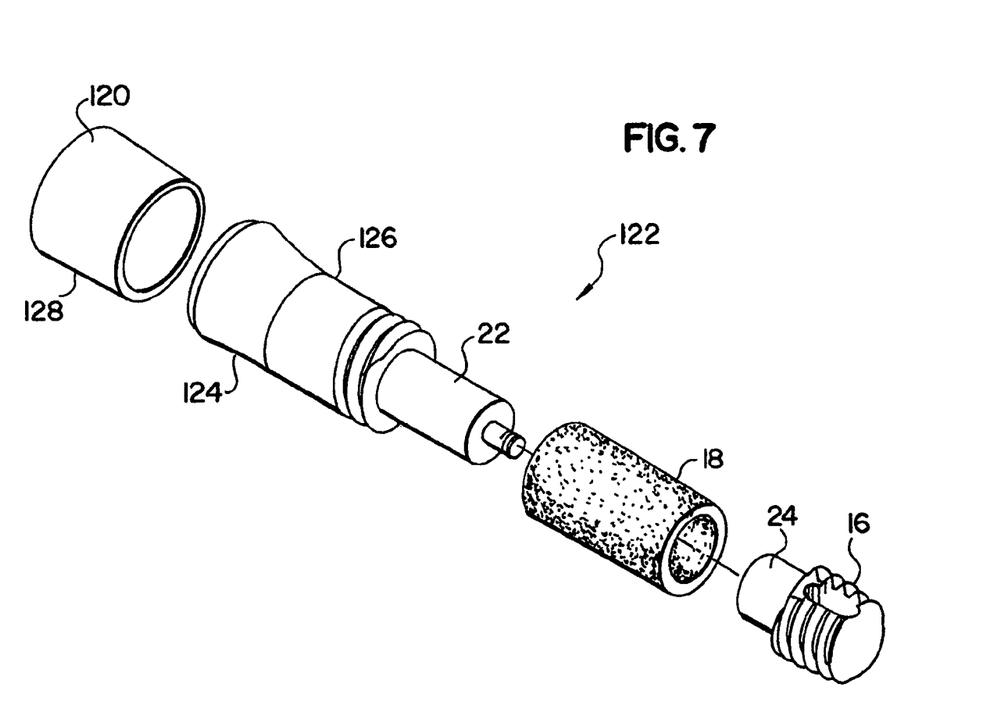
FIG. 7 is an exploded view of the dental implant of FIG. 6.

Referring to FIGS. 6 and 7, a collar 120 may optionally be used on an implant 122. While implant 122 may be similar to implant 10 of FIG. 1 or implant 60 of FIG. 4, implant 122 is shown here to be a single-stage surgery implant with an integral transgingival region 124. Otherwise, similar features are numbered the same as with the other implants. Collar 120 may be mounted on a head portion 126 by press fit, threading, adhesive, welding, connectors and so forth. The collar 120 may be a separate component from the head portion 126 or the collar 120 may be a surface treatment. The collar 120 may also be built-in to the head portion 126, i.e. the entire head portion 126 would be made up of the same material as the collar 120. The collar 120 has an exterior surface 128 configured to promote soft tissue attachment and may be made of high density polyethylene (HDPE), polyester, zirconium, ceramic or other similar surface treatments.

It will be understood that the structure for any of the implants disclosed herein can be applied to a single-stage surgery implant with a transgingival region 130—or a one-piece implant with an integral abutment 132—as shown in FIG. 1 in dashed lines for exemplary purposes.

While the illustrated forms are shown to be dental implants, it will be understood that such structures, with porous metal or porous tantalum portions cooperatively secured by an apical and coronal portion, may be applied to implants used on other areas of a human or animal body, whether or not such an implant is to be inserted into bone.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An implant extending along an axis, comprising:
    a head portion including a first externally threaded surface configured for engaging bone; a non-bone, porous intermediate portion, including:
        a bore axially extending throughout the intermediate portion, and
        a porous wall extending from a porous exterior surface of the intermediate portion to a porous interior surface of the intermediate portion, the porous interior surface defining a perimeter of the bore, wherein the perimeter defines a diameter of the bore that is substantially constant in an axial direction;
    an initially separate stem portion configured to engage the head portion so that at least the head portion and the stem portion cooperatively secure the intermediate portion on the implant without the intermediate portion being bonded to the head and stem portions, the stem portion including a second externally threaded surface configured for engaging bone;
    a core having a core diameter approximately equal to the diameter of the bore, the core extending axially from at least one of the head portion, the stem portion, and both the head and the stem portions.

2. The implant of claim 1, wherein the intermediate portion is porous for the ingrowth of bone.

3. The implant of claim 1, wherein the porous material includes tantalum.

4. The implant of claim 1, wherein the intermediate portion comprises pores that are at least partially filled with a filler material.

5. The implant of claim 4, wherein the filler material is a resorbable material.

6. The implant of claim 4, wherein the filler material is at least one of a resorbable polymer and a non-resorbable polymer.

7. The implant of claim 1, wherein the intermediate portion is made of at least one of a resorbable polymer, a non-resorbable polymer, synthetic bone material, and collagen.

8. The implant of claim 1, further comprising a locking mechanism configured to secure the head portion to the stem portion.

9. The implant of claim 8, wherein the locking mechanism is configured to secure the head portion to the stem portion by at least a press fit.

10. The implant of claim 8, wherein the locking mechanism includes threads on the head portion and the stem portion that mate with each other.

11. The implant of claim 8, wherein the porous portion comprises a sleeve portion.

12. The implant of claim 11, wherein the locking mechanism is formed on the core, and the core is configured at least partially extend into the sleeve portion.

13. The implant of claim 12, wherein the core is integrally formed with at least one of the head portion and the stem portion.

14. The implant of claim 12, wherein the core comprises a coronal portion extending from the head portion and an apical portion extending from the stem portion, and the coronal portion and the apical portion having engaging distal ends that form the locking mechanism.

15. The implant of claim 12, wherein the core has two opposite longitudinal ends, each end engaging an opposite one of the head portion and the stem portion.

16. The implant of claim 12, generally defining a longitudinal axis, and wherein the head portion and the stem portion each have a retaining shoulder extending radially outward from the core and relative to the axis, the shoulders facing each other and the sleeve portion assembled on the core to retain the sleeve portion between the shoulders.

17. The implant of claim 8, wherein the locking mechanism includes at least one axially extending post on one of the head portion and the stem portion, and at least one axially extending bore that receives the post on the other of the head portion and the stem portion.

18. The implant of claim 1, further comprising a collar mounted on the head portion, and the collar having an exterior surface configured to promote soft tissue attachment.

19. The implant of claim 1, wherein the stem portion comprises an opening for receiving bone while threading the implant into the bone.

20. The implant of claim 1, wherein the implant is a dental implant and the intermediate portion is configured to engage the mandible or maxilla.

21. The implant of claim 1, wherein the intermediate portion has a non-circular outer periphery.

22. The implant of claim 1, wherein the core is a non-threaded core, and wherein the intermediate portion extends around the core.

23. The implant of claim 22, wherein the intermediate portion is connected to the core solely by a friction fit.

24. The implant of claim 23, wherein a locking mechanism formed by the head portion and the stem portion retains the intermediate portion of the core.

25. The implant of claim 1, wherein at least one of the first externally threaded surface and the second externally threaded surface includes one or more self-tapping threads.

26. A method of assembling a dental implant, comprising:
placing, in an apical to coronal direction, a porous, non-bone sleeve on a core extending from at least one of a head portion and a separate stem portion wherein the head portion and the stem portion each include externally threaded surfaces for engaging, and threading the implant into bone, wherein the porous, non-bone sleeve includes a porous wall extending from an exterior surface to an interior surface, the interior surface defining a perimeter of a bore configured to be placed on the at least one of the head portion and the separate stem portion, the head portion and the stem portion each including a retaining shoulder extending radially outward from a longitudinal axis of the assembled dental implant, the perimeter of the bore defining a bore diameter approximately equal to a diameter of the core, wherein the bore diameter is substantially the same at a first location where the porous, non-bone sleeve engages the retaining shoulder of the head portion and at a second location where the porous, non-bone sleeve engages the retaining shoulder of the stem portion; and
engaging the stem portion to the head portion so that the head portion and the stem portion cooperatively secure the porous sleeve portion on the implant between the retaining shoulder of the head portion and the retaining shoulder of the stem portion without bonding the sleeve to the head and stem portions.

27. An implant extending along an axis, comprising:
a head portion including a first externally threaded surface configured for engaging bone; a non-bone, porous intermediate portion, including:
  a bore axially extending throughout the intermediate portion, the bore including a diameter that is substantially constant between a coronal end of the bore and an apical end of the bore, and
  a porous exterior surface including a continuous taper from a coronal end of the intermediate portion to an apical end of the intermediate portion;
an initially separate stem portion configured to engage the head portion so that at least the head portion and the stem portion cooperatively secure the intermediate portion on the implant without the intermediate portion being bonded to the head and stem portions, the head portion configured to engage the coronal end of the intermediate portion, the stem portion including a second externally threaded surface configured for engaging bone;
a core extending axially from at least one of the head portion, the stem portion, and both the head and the stem portions, the core defining a core diameter approximately equal to the bore diameter such that the core is configured to have a friction-fit with the non-bone, porous intermediate portion when engaged therewith.

* * * * *